United States Patent
Ferri et al.

(10) Patent No.: US 6,200,788 B1
(45) Date of Patent: Mar. 13, 2001

(54) β-KETOACYL-ACP SYNTHETASE II ENZYMES AND GENES CODING FOR SAME

(75) Inventors: Stefano R. Ferri, Verona (IT); Toshihiro Toguri, Yokohama (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 0 days.

(21) Appl. No.: 09/355,115

(22) PCT Filed: Jan. 20, 1998

(86) PCT No.: PCT/JP98/00194

§ 371 Date: Jul. 23, 1999

§ 102(e) Date: Jul. 23, 1999

(87) PCT Pub. No.: WO98/32770

PCT Pub. Date: Jul. 30, 1998

(30) Foreign Application Priority Data

Jan. 24, 1997 (JP) .................................................... 9-011430

(51) Int. Cl.⁷ .............................. C12N 9/00; C07H 21/00
(52) U.S. Cl. .......................................... 435/183; 536/23.1
(58) Field of Search ............................................. 435/183

(56) References Cited

FOREIGN PATENT DOCUMENTS

| | | |
|---|---|---|
| 6-500234 | 1/1994 | (JP) . |
| 6-504439 | 5/1994 | (JP) . |
| 7-501446 | 2/1995 | (JP) . |
| 92/03564 | 3/1992 | (WO) . |
| 92/13082 | 8/1992 | (WO) . |
| 93/10240 | 5/1993 | (WO) . |
| 95/18222 | 7/1995 | (WO) . |

OTHER PUBLICATIONS

Worsham, L., et al., "Early Catalytic Steps of *Euglena gracilis* Chloroplast Type II Fatty Acid Synthase," Biochem. Biophys. Acta., vol. 1170, No. 1, pp. 62–71 (1993).

Garwin, J.L., et al., "Structural, Enzymatic, and Genetic Studies of β–Ketoacyl–Acyl Carrier Protein Synthases I and II of *Escherichia coli*," Journal of Biological Chemistry, vol. 255, No. 24, pp. 11949–11956 (1980).

Magnuson, K., et al., "The Putative fabJ Gene of *Escherichia coli* Fatty Acid Synthesis in the fabF Gene," Journal of Bacteriology, vol. 177, No. 12, pp. 3593–3595 (1995).

Siggaard–Andersen, M., et al., "The fabJ–encoded β–ketoacyl–[acyl carrier protein] Synthase IV from *Escherichia coli* is Sensitive to Cerulenin and Specific for Short–Chain Substrates," Proc. Natl. Acad. Sci. USA, vol. 91, No. 23, pp. 11027–11031 (1994).

Shen, Z., et al., "Isolation of *Vibrio harveyi* Acyl Carrier Protein and the fabG, acpP, and fabF Genes Involved in Fatty Acid Biosynthesis," Journal of Bacteriology, vol. 178, No. 2, pp. 571–573 (1996).

GenBank Accession No. AAC43591, Feb. 1996.*

GenBank Accesion No. U39441, Feb. 1996.*

J. Ohlrogge and J. Browse, Lipid Biosynthesis, The Plant Cell, vol. 7, p. 957–970, Jul. 1995.

Browse et al., Gylcerolipid Synthesis: Biochemistry and Regulation, Annu. Rev. Plant Physiol. Plant Mol. Biol. pp. 42:467–506, 1991.

Wu et al., Elevated Levels of High–Melting–Point Phosphatidylglycerols Do Not Induce Chilling Sensitivity in an Arabidopsis Mutant, The Plant Cell, vol. 7, pp. 17–27, Jan. 1995.

* cited by examiner

*Primary Examiner*—Ponnathapu Achutamurthy
*Assistant Examiner*—Christian L. Fronda
(74) *Attorney, Agent, or Firm*—Foley & Lardner

(57) ABSTRACT

The object of the present invention is to provide a gene of a protein having an enzyme activity which makes it possible to regulate or control the content of saturated fatty acids and unsaturated fatty acids in plant cells, and an enzyme protein as the expression product.

There is disclosed a protein with a KASII enzyme activity which has a specific amino acid sequence, typically the amino acid sequence of a β-ketoacyl-ACP synthetase II (KASII) enzyme protein derived from cyanobacterium (*Anacystis nidulans*) or substantially the same amino acid sequence as the one described above.

There is also disclosed a KASII enzyme protein gene coding for the amino acid sequence of the above described protein.

Furthermore, there are disclosed a recombinant vector which comprises said gene, and a cell into which said gene has been introduced.

5 Claims, 3 Drawing Sheets

```
MTETGRQRVV ITGLGAITPI GNDPTEYWQG ILAGRNGIDL IRGFDASRHA CKIAGEVKDF
DPTQYMDRKD AKRMDRFAQL AVAASRQAVA DAKLDITELN ADAIGVLIGS GIGGLRVMED
QQTVLLEKGP DRCSPFMVPM MIANMAAGLT AIQLGAKGPC NVTVTACAAG SNAVGEAFRL
IQHGYAQAMI CGGTESCVTP LAMAGFAACK ALSLRNDDPA HACRPFDQGR DGFVMGEGAG
ILVLESLEHA QARGAHIYGE IVGYGMTCDA YHITSPVPGG LGAARAIEFG LRDANLQPSQ
VSYINAHGTS TPANDSTETA AIKKALGEHA YKTVISSTKS MTGHLLGGSG GIEAVAATLA
IAEDMVPPTI NLEDPDPDCD LDYVPNQARS LPVEVALSNS FGFGGHNVTL AFRKFHP
```

FIG. 1

```
                        10         20         30         40         50
BARLEY           MHAHAAHALGLRVPPPAFPRRRARPRRR---PAAAVLATSAAPQRE------TDP---RKRVV
                 ::   . :.:::..:  .:  ................:    ..:  ..:::
CASTOR-OIL PLANT PCSHYYSSNGLFPNTPLLPKRHPRLHHRLPRSGEAMAVAVQPEKEVATNKKPLMKQRRVV
                        80         90        100        110        120        130

60         70         80         90        100        110
BARLEY           ITGMGLASVFGSDVDTFYDRLLAGESGVGPIDRFDASSFPTRFAGQIRGFSSEGYIDGKN
                 :.:::::. .:  :.::...::.:.::...::::. . :::::.::.::.:... :
CASTOR-OIL PLANT VTGMGVVSPLGHDIDVYYNNLLDGSSGISQIDSFDCAQFPTRIAGEIKSFSTDGWVAPKL
                       140        150        160        170        180        190

120        130        140        150        160        170
BARLEY           DRRLDDCIRYCILSGKKALESAGLGAGSDAHVKLDVGRAGVLVGTGMGGLSVFSDGVQNL
                 ..:::. . : . .:::::::.. ..:   .::..:: .:::.::::.::..::.::::
CASTOR-OIL PLANT SKRMDKFMLYMLTAGKKALADGGI---TEDMMDELDKARCGVLIGSAMGGMKVFNDAIEAL
                       200        210        220        230        240

180        190        200        210        220        230
BARLEY           IEKGYRKISPFFIPYAITNMGSALLAIDVGFMGPNYSISTACATSNYCFYAAANHIRRGE
                 .X:::..::  .:.::::....:.:.:::.::::::::::::::::.. .::::: :::
CASTOR-OIL PLANT -RISYRKMNPFCVPFATTNMGSAMLAMDLGWMGPNYSISTACATSNFCILNAANHIIRGE
                      250        260        270        280        290        300

240        250        260        270        280        290
BARLEY           ADIIVAGGTEAAIIPIGLGGFVACRALSQRNDDPITACRPWDKERDGFVMGEGAGVLVME
                 :::: ::  ::.:::::::::::::::::::::::: . :::::.:::::::::::: :
CASTOR-OIL PLANT ADIMLCGGSDAAIIPIGLGGFVACRALSQRNDDPTKASRPWDMNRDGFVMGEGAGVLLLE
                       310        320        330        340        350        360

300        310        320        330        340        350
BARLEY           SLEHAMKRDAPIIAEYLGGAVNCDAYHMTDPRADGLGVSSCITMSLRDAGVAPEEVNYIN
                 .:::::. : :..:::.  .::::.::::::::::::::: ::::. ..:. ::::::::
CASTOR-OIL PLANT ELEHAKKRGANIYAEFLGGSFTCDAYHMTEPRPDGVGVILCIEKALARSGVSKEEVNYIN
                       370        380        390        400        410        420

360        370        380        390        400        410
BARLEY           AHATSTLAGDLAEVRAIKQVFKNPSEIKINSTKSMIGHCLGAAGGLEAIATIKSITTGWV
                 :::::: .:::  : ::..  ::... .. ............::::::::::.: ::::
CASTOR-OIL PLANT AHATSTPAGDLKEYEALMRCFSQNPDLRVNSTKSMIGHLLGAAGAVEAIATIQAIRTGWV
                       430        440        450        460        470        480

420        430        440        450        460
BARLEY           HPTINQFNPEPEVDFDTVANEKKQH-EVNVGISNSFGFGGHNSVVVFAPFK
                 :::.:: :::  .:::  ....:X.. ....:.:::::::::::. :::::
CASTOR-OIL PLANT HPNINLENPEEGVDTKVLVGPKKERLDIKVALSNSFGFGGHNSSIIFAPYK
                       490        500        510        520        530
```

FIG. 2

```
            10        20        30        40        50        60
Fab    MANLEKKRVVVTGLGAITPIGNTLQDYWQGLMEGRNGIGPITRFDASDQACRFGGEVKDF
       :.. ...X:..::::.::::::::.   .::::..:::::.   :   ::::  .::..:::::
KAS II MTETGRQRVVITGLGAITPIGNDPTEYWQGILAGRNGIDLIRGFDASRHACKIAGEVKDF
            10        20        30        40        50        60

70        80        90        100       110       120
Fab    DATQFLDRKEAKRMDRFCHFAVCASQQAINDAKLVINELNADEIGVLIGTGIGGLKVLED
       :.:::..:::.:::::::  .::  :::..::: :.::::::.:::  ::::::::.:.::
KAS II DPTQYMDRKDAKRMDRFAQLAVAASRQAVADAKLDITELNADAIGVLIGSGIGGLRVMED
            70        80        90        100       110       120

130       140       150       160       170       180
Fab    QQTILLDKGPSRCSPFMIPMMIANMASGLTAINLGAKGPNNCTVTACAAGSNAIGDAFRL
       :::::..:::::::::::::::::::::::::::::: :  ::::::::::::::.::::
KAS II QQTVLLEKGPDRCSPFMVPMMIANMAAGLTAIQLGAKGPCNVTVTACAAGSNAVGEAFRL
            130       140       150       160       170       180

190       200       210       220       230       240
Fab    VQNGYAKAMICGGTEAAITPLSYAGFASARALSFRNDDPLHASRPFDKDRDGFVMGEGSG
       .::.:::::::::::  .::::. ::::..::::::::.::.:::::.:::::::::: :
KAS II IQHGYAQAMICGGTESCVTPLAMAGFAACKALSLRNDDPAHACRPFDQGRDGFVMGEGAG
            190       200       210       220       230       240

250       260       270       280       290       300
Fab    ILILEELESALARGAKIYGEMVGYAMTCDAYHITAPVPDGRGATRAIAWALKDSGLKPEM
       :::::.::  :  ::::::::.::::::::::::::.:::::  : ::..:..:.  :.
KAS II ILVLESLEHAQARGAHIYGEIVGYGMTCDAYHITSPVPGGLGAARAIEFGLRDANLQPSQ
            250       260       270       280       290       300

310       320       330       340       350       360
Fab    VSYINAHGTSTPANDVTETRAIKQALGNHAYNIAVSSTKSMTGHLLGGSGGIEAVATVMA
       :::::::::::::::: ::: :::::::.::::.::.:::::::::::::::::::::::
KAS II VSYINAHGTSTPANDSTETAAIKKALGEHAYKTVISSTKSMTGHLLGGSGGIEAVAATLA
            310       320       330       340       350       360

370       380       390       400       410
Fab    IAEDKVPPTINLENPDPECDLDYVPGQSRALIVDVALSNSFGFGGHNVTLAFKKYQ
       ::::.:::::::::.:::.::::::.:.:::.:.:::::::::::::::::::X.:..
KAS II IAEDMVPPTINLEDPDPDCDLDYVPNQARSLPVEVALSNSFGFGGHNVTLAFRKFH
            370       380       390       400       410
```

FIG. 3

SEQUENCE LISTING

<160> NUMBER OF SEQ ID NOS: 11

<210> SEQ ID NO 1
<211> LENGTH: 1251
<212> TYPE: DNA
<213> ORGANISM: Anacystis nidulans

<400> SEQUENCE: 1

```
atgactgaaa ccggacgcca gcgtgttgtt attactggtt tgggagccat tactcccatc      60
ggtaatgatc aacggaata ttggcaggga atccttgccg gtcgcaacgg catcgatctg      120
attcggggct ttgatgcgtc tcgtcacgcc tgcaaaattg ccggggaggt caaggacttt      180
gaccccaccc agtacatgga ccgcaaggat gctaagcgga tggatcggtt tgcacaactg      240
gcggttgctg ccagtcgcca agcagtcgcc gatgccaagc tggacatcac tgaactgaat      300
gcggatgcga tcggggtgct gatcggctca ggcattggtg gtttgagggt gatggaggac      360
cagcagacgg ttttgctgga aaaggcccc gatcgctgca gcccttcat ggtgccgatg       420 atgatcgcca acatggcggc aggactgacg gccatccagt tgggtgccaa aggcccttgc      480
aatgtcacgg tgactgcttg cgctgcgggt tctaatgcgg tgggtgaagc cttccggctg      540
attcagcacg gctatgccca agccatgatc tgtggcggaa ctgaatcctg tgtgaccca       600 ctggctatgg ccggttttgc ggcctgtaag gcactgtcgc tgcgcaacga tgacccgcc      660 catgcttgcc gtcccttga ccaaggccgt gatggttttg tgatgggcga aggcgcaggg      720
```

-continued

```
attttggtct tggaatcctt ggagcatgcc caagcgaggg gcgctcacat ctatggcgaa     780
atcgtcggct atgcatgac ctgtgatgcc tatcacatca cctcgccggt cccaggtggt     840
ttgggtgcgg cccgggcgat cgagttcggg ctccgcgatg ccaatctgca gcccagccaa     900
gtcagctaca tcaatgctca cggcaccagc acaccggcca acgacagcac cgaaacggca     960
gctattaaga aagccctagg tgagcacgcc tacaaaaccg tgatcagctc gactaagtcg    1020
atgaccggtc acctgttagg gggctccggc ggaattgagg cggtagcggc aaccctcgcg    1080
atcgctgagg acatggtgcc gccgacgatt aacctggaag atcccgatcc cgattgcgac    1140
ttggactatg tccccaatca ggcgcgatcg ctaccggtgg aagtggcttt gtccaattcc    1200
ttcggctttg gtgggcacaa cgtcacgctg gccttccgga aattccatcc c             1251
```

<210> SEQ ID NO 2
<211> LENGTH: 417
<212> TYPE: PRT
<213> ORGANISM: Anacystis nidulans

<400> SEQUENCE: 2

```
Met Thr Glu Thr Gly Arg Gln Arg Val Val Ile Thr Gly Leu Gly Ala
 1               5                  10                  15

Ile Thr Pro Ile Gly Asn Asp Pro Thr Glu Tyr Trp Gln Gly Ile Leu
                20                  25                  30

Ala Gly Arg Asn Gly Ile Asp Leu Ile Arg Gly Phe Asp Ala Ser Arg
            35                  40                  45

His Ala Cys Lys Ile Ala Gly Glu Val Lys Asp Phe Asp Pro Thr Gln
        50                  55                  60

Tyr Met Asp Arg Lys Asp Ala Lys Arg Met Asp Arg Phe Ala Gln Leu
 65                  70                  75                  80

Ala Val Ala Ala Ser Arg Gln Ala Val Ala Asp Ala Lys Leu Asp Ile
                85                  90                  95

Thr Glu Leu Asn Ala Asp Ala Ile Gly Val Leu Ile Gly Ser Gly Ile
                100                 105                 110

Gly Gly Leu Arg Val Met Glu Asp Gln Gln Thr Val Leu Leu Glu Lys
            115                 120                 125

Gly Pro Asp Arg Cys Ser Pro Phe Met Val Pro Met Met Ile Ala Asn
        130                 135                 140

Met Ala Ala Gly Leu Thr Ala Ile Gln Leu Gly Ala Lys Gly Pro Cys
145                 150                 155                 160

Asn Val Thr Val Thr Ala Cys Ala Ala Gly Ser Asn Ala Val Gly Glu
                165                 170                 175

Ala Phe Arg Leu Ile Gln His Gly Tyr Ala Gln Ala Met Ile Cys Gly
            180                 185                 190

Gly Thr Glu Ser Cys Val Thr Pro Leu Ala Met Ala Gly Phe Ala Ala
        195                 200                 205

Cys Lys Ala Leu Ser Leu Arg Asn Asp Asp Pro Ala His Ala Cys Arg
    210                 215                 220

Pro Phe Asp Gln Gly Arg Asp Gly Phe Val Met Gly Glu Gly Ala Gly
225                 230                 235                 240

Ile Leu Val Leu Glu Ser Leu Glu His Ala Gln Ala Arg Gly Ala His
                245                 250                 255

Ile Tyr Gly Glu Ile Val Gly Tyr Gly Met Thr Cys Asp Ala Tyr His
            260                 265                 270

Ile Thr Ser Pro Val Pro Gly Gly Leu Gly Ala Ala Arg Ala Ile Glu
        275                 280                 285
```

```
Phe Gly Leu Arg Asp Ala Asn Leu Gln Pro Ser Gln Val Ser Tyr Ile
    290                 295                 300

Asn Ala His Gly Thr Ser Thr Pro Ala Asn Asp Ser Thr Glu Thr Ala
305                 310                 315                 320

Ala Ile Lys Lys Ala Leu Gly Glu His Ala Tyr Lys Thr Val Ile Ser
                325                 330                 335

Ser Thr Lys Ser Met Thr Gly His Leu Leu Gly Ser Gly Gly Ile
                340                 345                 350

Glu Ala Val Ala Ala Thr Leu Ala Ile Ala Glu Asp Met Val Pro Pro
                355                 360                 365

Thr Ile Asn Leu Glu Asp Pro Asp Pro Asp Cys Asp Leu Asp Tyr Val
    370                 375                 380

Pro Asn Gln Ala Arg Ser Leu Pro Val Glu Val Ala Leu Ser Asn Ser
385                 390                 395                 400

Phe Gly Phe Gly Gly His Asn Val Thr Leu Ala Phe Arg Lys Phe His
                405                 410                 415

Pro

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
ccacgtccag aaacgtccag aaacgtgaag tt                                    32

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
gaaggaaggt acgtaactta ctatactaac tgc                                   33

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
cgcacatatg actgaaaccg gacgcc                                           26

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
ccgcaagctt gcagcagcgc gtactgc                                          27
```

```
<210> SEQ ID NO 7
<211> LENGTH: 461
<212> TYPE: PRT
<213> ORGANISM: Barley

<400> SEQUENCE: 7

Met His Ala His Ala Ala His Ala Leu Gly Leu Arg Val Pro Pro Pro
 1               5                  10                  15

Ala Phe Pro Arg Arg Ala Arg Pro Arg Arg Pro Ala Ala Ala
             20                  25                  30

Val Leu Ala Thr Ser Ala Ala Pro Gln Arg Glu Thr Asp Pro Arg Lys
             35                  40                  45

Arg Val Val Ile Thr Gly Met Gly Leu Ala Ser Val Phe Gly Ser Asp
     50                  55                  60

Val Asp Thr Phe Tyr Asp Arg Leu Leu Ala Gly Glu Ser Gly Val Gly
 65                  70                  75                  80

Pro Ile Asp Arg Phe Asp Ala Ser Ser Phe Pro Thr Arg Phe Ala Gly
                 85                  90                  95

Gln Ile Arg Gly Phe Ser Ser Glu Gly Tyr Ile Asp Gly Lys Asn Asp
            100                 105                 110

Arg Arg Leu Asp Asp Cys Ile Arg Tyr Cys Ile Leu Ser Gly Lys Lys
        115                 120                 125

Ala Leu Glu Ser Ala Gly Leu Gly Ala Gly Ser Asp Ala His Val Lys
130                 135                 140

Leu Asp Val Gly Arg Ala Gly Val Leu Val Gly Thr Gly Met Gly Gly
145                 150                 155                 160

Leu Ser Val Phe Ser Asp Gly Val Gln Asn Leu Ile Glu Lys Gly Tyr
                165                 170                 175

Arg Lys Ile Ser Pro Phe Phe Ile Pro Tyr Ala Ile Thr Asn Met Gly
            180                 185                 190

Ser Ala Leu Leu Ala Ile Asp Val Gly Phe Met Gly Pro Asn Tyr Ser
        195                 200                 205

Ile Ser Thr Ala Cys Ala Thr Ser Asn Tyr Cys Phe Tyr Ala Ala Ala
    210                 215                 220

Asn His Ile Arg Arg Gly Glu Ala Asp Ile Ile Val Ala Gly Gly Thr
225                 230                 235                 240

Glu Ala Ala Ile Ile Pro Ile Gly Leu Gly Gly Phe Val Ala Cys Arg
                245                 250                 255

Ala Leu Ser Gln Arg Asn Asp Asp Pro Ile Thr Ala Cys Arg Pro Trp
            260                 265                 270

Asp Lys Glu Arg Asp Gly Phe Val Met Gly Glu Gly Ala Gly Val Leu
        275                 280                 285

Val Met Glu Ser Leu Glu His Ala Met Lys Arg Asp Ala Pro Ile Ile
290                 295                 300

Ala Glu Tyr Leu Gly Gly Ala Val Asn Cys Asp Ala Tyr His Met Thr
305                 310                 315                 320

Asp Pro Arg Ala Asp Gly Leu Gly Val Ser Ser Cys Ile Thr Met Ser
                325                 330                 335

Leu Arg Asp Ala Gly Val Ala Pro Glu Glu Val Asn Tyr Ile Asn Ala
            340                 345                 350

His Ala Thr Ser Thr Leu Ala Gly Asp Leu Ala Glu Val Arg Ala Ile
        355                 360                 365

Lys Gln Val Phe Lys Asn Pro Ser Glu Ile Lys Ile Asn Ser Thr Lys
    370                 375                 380
```

-continued

```
Ser Met Ile Gly His Cys Leu Gly Ala Ala Gly Gly Leu Glu Ala Ile
385                 390                 395                 400

Ala Thr Ile Lys Ser Ile Thr Thr Gly Trp Val His Pro Thr Ile Asn
                405                 410                 415

Gln Phe Asn Pro Glu Pro Glu Val Asp Phe Asp Thr Val Ala Asn Glu
            420                 425                 430

Lys Lys Gln His Glu Val Asn Val Gly Ile Ser Asn Ser Phe Gly Phe
        435                 440                 445

Gly Gly His Asn Ser Val Val Val Phe Ala Pro Phe Lys
    450                 455                 460

<210> SEQ ID NO 8
<211> LENGTH: 468
<212> TYPE: PRT
<213> ORGANISM: Castor bean

<400> SEQUENCE: 8

Pro Cys Ser His Tyr Tyr Ser Ser Asn Gly Leu Phe Pro Asn Thr Pro
  1               5                  10                  15

Leu Leu Pro Lys Arg His Pro Arg Leu His His Arg Leu Pro Arg Ser
            20                  25                  30

Gly Glu Ala Met Ala Val Ala Val Gln Pro Glu Lys Glu Val Ala Thr
        35                  40                  45

Asn Lys Lys Pro Leu Met Lys Gln Arg Arg Val Val Val Thr Gly Met
     50                  55                  60

Gly Val Val Ser Pro Leu Gly His Asp Ile Asp Val Tyr Tyr Asn Asn
 65                  70                  75                  80

Leu Leu Asp Gly Ser Ser Gly Ile Ser Gln Ile Asp Ser Phe Asp Cys
                 85                  90                  95

Ala Gln Phe Pro Thr Arg Ile Ala Gly Glu Ile Lys Ser Phe Ser Thr
            100                 105                 110

Asp Gly Trp Val Ala Pro Lys Leu Ser Lys Arg Met Asp Lys Phe Met
        115                 120                 125

Leu Tyr Met Leu Thr Ala Gly Lys Lys Ala Leu Ala Asp Gly Gly Ile
    130                 135                 140

Thr Glu Asp Met Met Asp Glu Leu Asp Lys Ala Arg Cys Gly Val Leu
145                 150                 155                 160

Ile Gly Ser Ala Met Gly Gly Met Lys Val Phe Asn Asp Ala Ile Glu
                165                 170                 175

Ala Leu Arg Ile Ser Tyr Arg Lys Met Asn Pro Phe Cys Val Pro Phe
            180                 185                 190

Ala Thr Thr Asn Met Gly Ser Ala Met Leu Ala Met Asp Leu Gly Trp
        195                 200                 205

Met Gly Pro Asn Tyr Ser Ile Ser Thr Ala Cys Ala Thr Ser Asn Phe
    210                 215                 220

Cys Ile Leu Asn Ala Ala Asn His Ile Ile Arg Gly Glu Ala Asp Ile
225                 230                 235                 240

Met Leu Cys Gly Gly Ser Asp Ala Ala Ile Ile Pro Ile Gly Leu Gly
                245                 250                 255

Gly Phe Val Ala Cys Arg Ala Leu Ser Gln Arg Asn Asp Asp Pro Thr
            260                 265                 270

Lys Ala Ser Arg Pro Trp Asp Met Asn Arg Asp Gly Phe Val Met Gly
        275                 280                 285

Glu Gly Ala Gly Val Leu Leu Leu Glu Glu Leu Glu His Ala Lys Lys
```

```
            290                 295                 300
Arg Gly Ala Asn Ile Tyr Ala Glu Phe Leu Gly Gly Ser Phe Thr Cys
305                 310                 315                 320

Asp Ala Tyr His Met Thr Glu Pro Arg Pro Asp Gly Val Gly Val Ile
                325                 330                 335

Leu Cys Ile Glu Lys Ala Leu Ala Arg Ser Gly Val Ser Lys Glu Glu
                340                 345                 350

Val Asn Tyr Ile Asn Ala His Ala Thr Ser Thr Pro Ala Gly Asp Leu
                355                 360                 365

Lys Glu Tyr Glu Ala Leu Met Arg Cys Phe Ser Gln Asn Pro Asp Leu
                370                 375                 380

Arg Val Asn Ser Thr Lys Ser Met Ile Gly His Leu Leu Gly Ala Ala
385                 390                 395                 400

Gly Ala Val Glu Ala Ile Ala Thr Ile Gln Ala Ile Arg Thr Gly Trp
                405                 410                 415

Val His Pro Asn Ile Asn Leu Glu Asn Pro Glu Glu Gly Val Asp Thr
                420                 425                 430

Lys Val Leu Val Gly Pro Lys Lys Glu Arg Leu Asp Ile Lys Val Ala
                435                 440                 445

Leu Ser Asn Ser Phe Gly Phe Gly Gly His Asn Ser Ser Ile Ile Phe
                450                 455                 460

Ala Pro Tyr Lys
465

<210> SEQ ID NO 9
<211> LENGTH: 416
<212> TYPE: PRT
<213> ORGANISM: Synechocystis sp.

<400> SEQUENCE: 9

Met Ala Asn Leu Glu Lys Lys Arg Val Val Thr Gly Leu Gly Ala
 1               5                  10                  15

Ile Thr Pro Ile Gly Asn Thr Leu Gln Asp Tyr Trp Gln Gly Leu Met
                20                  25                  30

Glu Gly Arg Asn Gly Ile Gly Pro Ile Thr Arg Phe Asp Ala Ser Asp
                35                  40                  45

Gln Ala Cys Arg Phe Gly Gly Glu Val Lys Asp Phe Asp Ala Thr Gln
    50                  55                  60

Phe Leu Asp Arg Lys Glu Ala Lys Arg Met Asp Arg Phe Cys His Phe
65                  70                  75                  80

Ala Val Cys Ala Ser Gln Gln Ala Ile Asn Asp Ala Lys Leu Val Ile
                85                  90                  95

Asn Glu Leu Asn Ala Asp Glu Ile Gly Val Leu Ile Gly Thr Gly Ile
                100                 105                 110

Gly Gly Leu Lys Val Leu Glu Asp Gln Gln Thr Ile Leu Leu Asp Lys
            115                 120                 125

Gly Pro Ser Arg Cys Ser Pro Phe Met Ile Pro Met Met Ile Ala Asn
        130                 135                 140

Met Ala Ser Gly Leu Thr Ala Ile Asn Leu Gly Ala Lys Gly Pro Asn
145                 150                 155                 160

Asn Cys Thr Val Thr Ala Cys Ala Ala Gly Ser Asn Ala Ile Gly Asp
                165                 170                 175

Ala Phe Arg Leu Val Gln Asn Gly Tyr Ala Lys Ala Met Ile Cys Gly
                180                 185                 190
```

-continued

```
Gly Thr Glu Ala Ala Ile Thr Pro Leu Ser Tyr Ala Gly Phe Ala Ser
            195                 200                 205

Ala Arg Ala Leu Ser Phe Arg Asn Asp Asp Pro Leu His Ala Ser Arg
    210                 215                 220

Pro Phe Asp Lys Asp Arg Asp Gly Phe Val Met Gly Glu Gly Ser Gly
225                 230                 235                 240

Ile Leu Ile Leu Glu Glu Leu Glu Ser Ala Leu Ala Arg Gly Ala Lys
                245                 250                 255

Ile Tyr Gly Glu Met Val Gly Tyr Ala Met Thr Cys Asp Ala Tyr His
            260                 265                 270

Ile Thr Ala Pro Val Pro Asp Gly Arg Gly Ala Thr Arg Ala Ile Ala
        275                 280                 285

Trp Ala Leu Lys Asp Ser Gly Leu Lys Pro Glu Met Val Ser Tyr Ile
    290                 295                 300

Asn Ala His Gly Thr Ser Thr Pro Ala Asn Asp Val Thr Glu Thr Arg
305                 310                 315                 320

Ala Ile Lys Gln Ala Leu Gly Asn His Ala Tyr Asn Ile Ala Val Ser
                325                 330                 335

Ser Thr Lys Ser Met Thr Gly His Leu Leu Gly Gly Ser Gly Gly Ile
            340                 345                 350

Glu Ala Val Ala Thr Val Met Ala Ile Ala Glu Asp Lys Val Pro Pro
        355                 360                 365

Thr Ile Asn Leu Glu Asn Pro Asp Pro Glu Cys Asp Leu Asp Tyr Val
    370                 375                 380

Pro Gly Gln Ser Arg Ala Leu Ile Val Asp Val Ala Leu Ser Asn Ser
385                 390                 395                 400

Phe Gly Phe Gly Gly His Asn Val Thr Leu Ala Phe Lys Lys Tyr Gln
                405                 410                 415
```

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: synthetic peptide

<400> SEQUENCE: 10

```
Glu Glu Val Asn Tyr Ile Asn Ala
  1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: synthetic peptide

<400> SEQUENCE: 11

```
Asn Ser Phe Gly Phe Gly Gly
  1               5
```

β-KETOACYL-ACP SYNTHETASE II ENZYMES AND GENES CODING FOR SAME

TECHNICAL FIELD

The present invention relates to the amino acid sequence of a synthetase capable of synthesizing fatty acids in plants and the structure of DNA related to the same, that is to say, a fatty acid synthesizing enzyme protein having a specific amino acid sequence, and a gene coding for it. Cells can be transformed with such a gene and chimera genes in which an appropriate regulatory sequence (regulatory gene) has been inserted to control the amounts of saturated and unsaturated fatty acids in the cell.

BACKGROUND ART

Fatty acid synthases are known to be divided into two types; the enzymes in animals and yeasts are fatty acid synthetase complexes (FAS) in which a variety of enzymes are wholly linked as a complex having a single function (type I), while those in higher plant cells and procaryotes are of such type that each of the enzymes become independently disconnected outside the organisms (type II). An acyl carrier protein (ACP) which is a soluble protein is required for the synthesis of a fatty acid with the enzyme type II, and the fatty acids are synthesized as an acyl-ACP. The final product of the synthesis system is palmitoyl-ACP. The palmitoyl-ACP is further converted into stearoyl-ACP by chain elongation before desaturation with a soluble fatty acid desaturase (stearoyl-ACP desaturase) to lead to oleoyl-ACP. Palmitic acid and oleic acid are incorporated into polar lipid, and then the latter is further desaturated (J. Ohlrogge and J. Browse (1995) Lipid Biosynthesis. The Plant Cell, 7, p. 957–970).

The chain elongation enzyme which catalyzes the chain elongation from palmitoyl-ACP to stearoyl-ACP produces stearoyl-ACP from palmitoyl-ACP, malonyl-ACP and NADPH (J. Ohlrogge and J. Browse (1995) Lipid Biosynthesis. The Plant Cell, 7, p. 957–970). These reactions describe the total scheme of a series of enzyme reactions for the production of a stearoyl-thioester by the reduction, dehydration and further reduction of the condensation product of a palmitoyl-thioester and the C2 unit.

Lipid biosynthesis in plants has been studied very extensively (Browse et al., Annu. Rev. Plant Physiol. Mol. Biol. (1991) 42: 467–506). It has been elucidated from these researches that the production of stearic acid starting from palmitic acid in plant cells is a reaction catalyzed by the enzyme β-ketoacyl-ACP synthetase II (KASII). However, there has been described in the aforementioned publication the isolation of neither the enzyme KASII or its gene, and thus their sequences remain unknown.

Three isozymes of KAS have been found in chloroplast in plants. Among the two isozymes other than KASII, the isozyme KASIII catalyzes the initiation of the synthesis of an acyl chain, while the isozyme KASI catalyzes the elongation reaction of an acyl chain to the palmitoyl-ACP with 16 carbon atoms. A variety of mutants of enzymes involved in the lipid synthesis of plants have been isolated from Arabidopsis, among which the enzymes responsible for the desaturation reaction have been studied extensively. There have also been described for the KASII, the mutant of which has been designated as fab1. In this mutant, the KASII enzyme activity was lowered to 65%, and thus the palmitic acid content increased by 7% in leaves and 3% in roots (Wu et al., Plant Physiol. (1994) 106: 143–150). As regards the complete purification of the enzyme KASII, genes have been cloned from a castor bean (*Ricinus communis*; Japanese Patent Laid-Open Publication No. 500234/1994) and soybean (*Glycine max*; Japanese Patent Laid-Open Publication No. 501446/1995) on the basis of the amino acid sequences of the limitedly degraded peptide of the purified enzyme. In the above described publications, as regards the changes of fatty acids by transformation with these genes, the C16 fatty acid content on the expression of the gene of the castor bean in *E. coli* was decreased by ca. 20% thus corresponding to a little over 30% of the total fatty acid content, while on introducing the soybean gene into canola the palmitic acid content in the seeds was decreased by 0.8% and on introducing the gene into tobacco the palmitic acid content in the leaves was decreased by ca. 2%. In this connection, no sequence exhibiting distinct homology has been curiously found between the genes of the castor bean and soybean.

By the way, it has been known that in membrane lipids constituting biomembrane, the phase transition temperature varies primarily depending on the unsaturation degrees of the fatty acid linked to the lipid, and as a result the chilling resistance of the organism also varies. It is thought that the unsaturation degree of the membrane lipid is effectively increased with an enzyme such as fatty acid acyltransferase (PCT/JP 92/00024 (PCT/WO 92/13082)), fatty acid desaturase (PCT/JP 94/02288 (PCT/WO 95/18222)).

DISCLOSURE OF THE INVENTION

In consideration of the above described situations, the object of the present invention is to provide a gene of a protein having an enzyme activity which makes it possible to regulate or control the content of saturated fatty acids and unsaturated fatty acids in plant cells or microorganism cells and an enzyme protein as the expression product.

It is believed that if there is a protein having such an enzyme activity that the decrease of the enzyme activity responsible for the synthesis of fatty acids leads to the increase of the palmitic acid content in lipids of cells while the increase of enzyme activity leads to the increase of content of the fatty acids with 18 or more carbon atoms, the unsaturated fatty acid contents in the lipids is possibly increased for example as a result of the increase of content of the fatty acids with 18 or more carbon atoms due to the increase of the enzyme activity.

The present inventors have conducted earnest researches in order to solve the above described problems, and as a result, successfully isolated a gene which codes for an enzyme β-ketoacyl-ACP synthetase II (KASII) from cyanobacterium (*Anacystis nidulans*), and found that the introduction of the gene into *E. coli* confers the KASII producing ability whereby fatty acids having extended in chain length increase. The present invention has been accomplished on the basis of the finding.

That is, the present invention relates to the protein which has an amino acid sequence represented by SEQ ID NO. 2 or substantially the same amino acid sequence as the one represented by SEQ ID NO. 2 and exhibit the KASII enzyme activity.

The present invention also relates to the KASII enzyme gene coding for the protein which has an amino acid sequence represented by SEQ ID NO. 2 or substantially the same amino acid sequence as the one represented by SEQ ID NO.2 and exhibit the KASII enzyme activity.

Furthermore, the present invention relates to the recombinant vector containing the gene and the cells in which the gene has been introduced.

BRIEF DESCRIPTION OF THE DRAWINGS

FIG. 1 shows the amino acid sequence represented by single-letter codes corresponding to SEQ ID NO.2 (three-letter codes amino acid).

FIG. 2 illustrates the comparative chart of the amino acid sequence (SEQ ID NO:9) of barley (Accession No. P23902 in SWISS-PROT data base) KASI enzyme with the amino acid sequence (SEQ ID NO:8) expected from the DNA sequence of the castor bean (GENBANK Accession No. L13241) KASII enzyme.

FIG. 3 illustrates the comparative chart of the amino acid sequence (SEQ ID NO:2) of the enzyme KASI (referred to as KASII in the drawing) derived from *Anacystis nidulans* in the present invention with the amino acid sequence (SEQ ID NO:9) (referred to as Fab) of fabF or J (code S11 1069) of Synechocystis sp. Strain PCC6803.

BEST MODE FOR CARRYING OUT THE INVENTION

The present invention is now explained in detail as follows.

KASII enzyme active protein and its gene

As described above, the protein of the present invention having the KASI enzyme activity has the amino acid sequence represented by SEQ ID NO. 2 (corresponding to the amino acid sequence (single-letter code) in FIG. 1) or substantially the same amino acid sequence as the one represented by SEQ ID NO. 2, and the gene of the KASII enzyme active protein according to the present invention codes for the above described protein having the amino acid sequence represented by SEQ ID NO. 2 or substantially the same amino acid sequence as the one represented by SEQ ID NO. 2. The phraseology "protein having the KASII enzyme activity" or "KASII enzyme active protein" in the present invention means the protein having an enzyme activity which produces a longer fatty acid (particularly stearic acid) by extending the chain length of a fatty acid (particularly palmitic acid).

As the KASII enzyme active proteins described above, there can be used in the present invention an appropriate naturally occurring gene products as well as mutant gene products in which a part of the amino acid sequences of the proteins has been mutated, provided that the proteins have the above described KASII enzyme activity. By way of example, the product of the KASII enzyme active protein gene typically includes the KASII enzyme derived from the cyanobacterium as a microorganism (SEQ ID NO. 2).

The phrase substantially the same amino acid sequence, in the present invention means that the sequence of the mutant described above is also included, such as typically the amino acid sequence of the enzyme protein derived from the cyanobacterium represented by SEQ ID NO. 2 (SEQ ID NO. 2, FIG. 1) or the sequence in which one or more, preferably one or a few amino acids have been substituted, deleted, inserted or added.

Therefore, the term "substantially" in the case of "the gene coding for . . . substantially the same amino acid sequence" in the present invention is intended to include not only the gene of a DNA sequence coding for the naturally occurring protein having the KASII enzyme activity defined above, but also the gene of a DNA sequence coding for the mutant KASII enzyme active protein described above, typically the gene of the DNA sequence coding for the amino acid sequence represented by SEQ ID NO. 2 or the amino acid sequence in which one or more, preferably one or a few amino acids are substituted, deleted, inserted or added. Also, it goes without saying that when a DNA chain generally codes for a polypeptide having an amino acid sequence, plural gene codes (codons) corresponding to an amino acid are present (degenerated mutants), and thus any gene codes can be used also in the DNA chain coding for the KASII enzyme active protein of the present invention.

The KASII enzyme active protein encoded by the gene of the present invention has a function of the chain elongation enzyme for the fatty acid synthesis which is originally present in plants and microorganisms as described above, and thus, in the further specific function, has an enzyme activity for producing a longer fatty acid (particularly, stearic acid) that the chain length of a fatty acid (particularly, palmitic acid) has been elongated. The typical example of the protein according to the present invention is the one derived from cyanobacterium. The chemical structure of the enzyme KASII derived from the cyanobacterium is locally similar to the protein encoded by the KASII gene of *E. coli* and barley, and also similar to the enzyme derived from the castor bean among the patent publications regarding to the above described KASII. The KASII enzyme active protein according to the present invention has, as described above, the amino acid sequence represented by SEQ ID NO. 2 or substantially the same amino acid sequence as the above described one, and a markedly high enzyme activity for producing a longer fatty acid (particularly, stearic acid) in which the chain length of a fatty acid (particularly, palmitic acid) has been elongated.

While a means for obtaining the gene coding for the protein of the present invention is the chemical synthesis of at least a part of the chain according to the method of nucleic acid synthesis, it is more preferable in consideration of the number of the amino acids to be linked to use the method, rather than the chemical synthesis, in which cDNA is synthesized from mRNA isolated from a naturally occurring material, in particular cyanobacterium as a bacterium, and the gene is obtained from the gene library by the method commonly used in the field of genetic engineering.

The gene of the enzyme KASII can be obtained for example as follows.

Firstly, the enzyme from a higher plant or a microorganism, particularly cyanobacterium is purified by the known method, and fragmented with peptidase to determine the amino acid sequences of the fragments. Oligonucleotides corresponding to the fragmented peptides whose amino acid sequence has been determined are then synthesized. The total RNA is separately extracted from the plant or the microorganism, and the DNA complementary to the RNA (CDNA) is synthesized. The CDNA is linked to an appropriate vector such as phage λgt11 to make the CDNA library. In this connection, as the method for screening the gene, the conventional methods, for example immunological methods such as the plaque hybridization method with antibody or the colony hybridization method, or the hybridization method with nucleotide probe or the like can be used.

It is also possible to obtain the target sequence by designing primers corresponding to the short DNA sequences positioned at both of the ends of the aimed sequence on the basis of the consensus sequence of a known KASII enzyme or of the other isozyme related to it, and conducting PCR with DNA obtained from a material used for determining the total sequence as a template. In this case, the activity can be identified for example by expressing the KAS gene in *E. coli* in order to discriminating the isozyme of the gene.

The DNA sequence of the gene according to the present invention in the clone thus screened can be determined and confirmed generally by the known methods such as the dideoxynucleotide chain terminating method with M13 phage (Sambrook et al., Molecular Cloning, 2nd edition (1989)).

The present gene of which DNA sequence has been determined as described above can be also synthesized generally by the known means, for example a commercially available DNA synthesizer by the phosphite method.

Also, for expressing a DNA chain or its fragment to produce a protein or a polypeptide encoded thereby, an expression regulatory sequence is required in addition to the DNA sequence (coding region) corresponding to the amino acid sequence. Thus, the DNA chain of the present invention includes the DNA sequence comprising such expression regulatory sequence. Among the expression regulatory region, an important one particularly for expressing it in a higher plant is the promoter sequence upstream of the coding region (e.g. derived from the 35S promoter of cauliflower mosaic virus), and the poly A addition signal downstream (e.g. derived from the terminator of nopaline synthesis enzyme). When DNA obtained is the genome gene of a higher plant, it can also be used directly provided that the DNA sequence comprises expression regulatory region.

Use of KASII enzyme active protein gene

As described above, the present invention relates also to the recombinant vector comprising the above described DNA chain or its fragment, and to cells into which the gene has been introduced.

The recombinant vector is a vector to which the above described DNA chain or its fragment has been linked, and there can be used the known vector such as plasmid (e.g. pET17b), phage (e.g. λZAPII).

The enzyme KASII can be produced in a host such as an appropriate plant or microorganism cells as described above by introducing the recombinant vector DNA into the host for expression.

In this connection, although the cells may be either microorganism cells or plant cells irrespective of the kind of organisms, the microorganism cells include *E. coli* and the like, and the plant cells include chilling sensitive plants such as tobacco and the like. The gene can be introduced into plants generally with the known methods such as the ones described in "Plant Molecular Biology Manual, Second Edition; S. G. Gelvin, and R. A. Schilperoort eds, Kluwer Academic Publishers, 1995". By way of example, there can be mentioned the biological methods which include a method with virus or a method with Agrobacterium, and the physicochemical methods which include the electroporation method, the polyethylene glycol method, the particle gun method, and the like.

Also, the enzyme KASII is a protein which is present in chloroplast envelope in plants, so that it is necessary to attach the DNA chain coding for transit peptide to the chloroplast upstream the enzyme KASII. By way of example, the small sub-unit gene of ribulose-1,5-bisphosphate carboxylase of pea can be used as a gene coding for the transit peptide.

The KASII enzyme active protein of the present invention, typically the gene coding for the KASII enzyme active protein (amino acid SEQ ID NO. 2) derived from the cyanobacterium *Anacystis nidulans* (the DNA sequence of the gene derived from the cyanobacterium is represented by SEQ ID NO. 1) is useful for the improvement of lipid composition in plants and microorganisms by transformation, particularly the control of the amount ratio between fatty acids with 16 and 18 carbon atoms.

The expression of the KASII enzyme protein of the present invention as a foreign protein in an organism leads to the elongation of the chain length of fatty acids from 16 carbon atoms (palmitic acid) to the 18 carbon atoms (stearic acid), the stearic acid is desaturated in an organism, and the content of unsaturated fatty acids is increased. It is believed that chilling resistance is enhanced in plants in which unsaturated fatty acids have been increased (PCT/WO 92/13082, PCT/WO 95/18222), and it is expected that the resistance to the stress of culture is enhanced in microorganisms (yeast, *E. coli* and the like) in which unsaturated fatty acids have been increased.

EXAMPLES

The present invention is described below in detail with reference to examples, it is not to be limited by these examples.

Example 1

Preparation of DNA derived from *A. nidulans*, and preparation of DNA library

*A. nidulans* (Catalog No. IAM M-6: it is possible to obtain it from Institute of Molecular Cytology, Tokyo University) was cultured in about 100 ml of the BG-11 culture medium prepared according to the method described in p. 279 of Plant Molecular Biology, by Shaw (IRL PRESS, 1988). The bacterial cells were cultured sufficiently by shaking at 120 times/min under a fluorescent light of 1000 lux at 25° C. The cells were recovered by centrifugation at 5,000 g for 10 min. at room temperature.

In order to isolate DNA, the precipitated cells were suspended in 50 ml of 50 mM Tris Cl (pH 8.0), 1 mM EDTA (solution A) and washed by centrifugation again. The cells were then re-suspended again in 15 ml (solution) of 50 mM Tris Cl (pH 8.0), 20 mM EDTA, 50 mM NaCl, 0.25 M sucrose (Solution B), to which 40 mg of lysozyme (Sigma) dissolved in Solution B was added, and the mixture was shaked slowly at 37° C. After 1 hour, 15 mg of proteinase K and SDS at a final concentration of 1% were added, and the mixture was shaked slowly over night at 37° C. Next day, $NaClO_4$ was adjusted to a concentration of 1 M, 20 ml of chloroform/isoamyl alcohol (24:1) was added, the mixture was shaked slowly for 10 minutes, and the aqueous layer was separated by centrifugation. After extraction with chloroform/isoamyl alcohol was repeated once again, 50 ml of ethanol was added, and DNA was recovered by winding it around a glass rod. The DNA was dissolved in 20 ml of solution A, NaCl was adjusted to a concentration of 0.1 M, RNase at a concentration of 50 mg/ml was added and the reaction was conducted at 37° C. for 1 hour. The reaction mixture was then subjected to an extraction twice with an equivalent amount of phenol saturated with solution A. After DNA in the aqueous layer was recovered by the addition of ethanol and washed with 70% ethanol, it was dissolved in 1 ml of solution A to prepare the DNA solution.

After partial digestion of ca. 100 g of DNA with Sau 3A I for the purpose of preparing a genomic DNA library from DNA thus obtained, DNA of about 9–23 kb was collected by ultracentrifugation on a gradient of sucrose density according to the method described by Sambrook et al. It was cloned into DASH II (kit by Stratagene) cleaved with Bam HI and Hind III.

Example 2

Cloning of KASII enzyme-like gene from cyanobacterium *Anacystis nidulans*

Several short DNA chains were synthesized by comparing the enzyme KASI of barley with the enzyme KASII of castor bean while paying attention to the regions having high homology between these enzymes (FIG. 2). Among these chains, distinct bands in accordance with expected sizes were observed in reactions carried out with the following combination.

1: 5'-CC(ACGT)CC(AG)AA(ACGT)CC(AG)AA(ACGT)GA(AG)TT-3' (SEQ ID NO. 3)

2: 5'-GA(AG)GA(AG)GT(ACGT)AA(CT)TA(CT)AT(ACT)AA(CT)GC-3' (SEQ ID NO. 4)

Among the sequences, SEQ ID NO. 4 is a sense primer corresponding to the amino acid sequence (SEQ ID NO:10) EEVNYINA, and SEQ ID NO. 3 is a primer coding for the anti-sense chain corresponding to the amino acid sequence (SEQ ID NO:11) NSFGFGG. The PCR reactions were carried out with the sense and anti-sense primers. The reaction was performed under a condition of using a Gene-Amp™ PCR kit (Takara Shuzo Co., Ltd.) by adding in 100 µl of reaction solution 20 µM of the primers, respectively, and 1 µg of DNA derived from *A. nidulans*. The reaction program of 35 cycles was performed with each cycle comprising the reaction at 95° C. (1 minute), 50° C. (1 minute) and 72° C. (2 minutes), provided that only in the first cycle, the reaction at 95° C. was extended to 3 minutes and the reaction temperature at 50° C. was changed into 35° C. After completion of reaction, the reaction mixture was subjected to extraction with 100 µl of chloroform to recovered the aqueous layer and chloroform was then removed with 100 µl of ether to give an aqueous layer, from which 10 µl portion was analyzed by 2% agarose gel electrophoresis.

As a result, DNA having the same size as the expected one (ca. 330 bp) was detected. The DNA fragment was cloned into a PCRII vector (Invitrogen Co.). The DNA sequence was determined by the dideoxy method with use of a fluorescent sequencer (manufactured by Applied Biosystem Co.). The DNA was labeled with 32P-dCTP using Multiprime DNA labelling kit (Amersham Co.) to prepare a probe and used for the following experiment of hybridization.

*E. coli* P2392 was infected with a phage in the DNA library and ca. 10,000 plaques were formed on a plate having a diameter of ca. 15 cm and containing an NZYM medium, which were transferred onto a nylon membrane. Hybridization was carried out by the method described by Sambrook et al. (Molecular Cloning; Second edition, Cold Spring Harbor Laboratory Press, 1989) under a condition in a solution consisting of 5× SSC (1× SSC comprising 0.15 M NaCl and 15 mM sodium citrate), 10 mM EDTA, 10× Denhardt solution (50× Denhardt solution comprising Ficoll (Type 400, Pharmacia Co.), polyvinyl pyrrolidone, bovine serum albumin (fraction V, Sigma Co.), respectively, in an amount of 10 g/l), and 250 µg/ml of salmon sperm DNA at 60° C. for 16 hours. Thereafter, the membrane was washed twice with 5× SSC and 0.1% SDS solution at 45° C. for 15 minutes and subjected to autoradiography. Ten positive clones were purified to obtain the phage DNAs, which were cleaved with some restriction enzymes, subjected to agarose gel electrophoresis followed by Southern blotting on a nylon membrane according to the conventional method. The membrane was hybridized under the same condition as the above described plaque hybridization to compare the hybridization strengths and the DNA fragment lengths. As a result, the two clones of them (λB, F) were believed to be satisfactory from the standpoint of both strength and fragment length, and thus cleaved further with some restriction enzymes to carry out Southern hybridization. As a result, a hybridizing fragment having a length of about 5 kbp was detected by cleaving with Sal I, so that it was subcloned to the Sal I site of pUC 19 (Takara Shuzo Co., Ltd.) (referred to as pB and pF, respectively). When each clone was subjected in more detail to mapping with restriction enzymes, pB and pF were judged as the identical DNA. Thus, a deletion plasmid on the latter was prepared with restriction enzyme according to the conventional method, and the base sequence of the DNA chain for about 2 kbp fragment comprising the hybridizing DNA fragment was determined with a fluorescent sequencer (SEQ ID NO. 1). An open reading frame (ORF) consisting of 1251 bp was found from it, and an amino acid sequence having 417 residues was presumed (SEQ ID NO. 2). Comparing the amino acid sequence with that of proteins registered to database for homology, it exhibited significant homology with a fatty acid synthase. In particular, it exhibited the highest homology of 74% with the protein which was thought to be fabF or J in the total genome sequence for Synechocystis sp. strain PCC6803 prepared by KAZUSA DNA Institute (database DDBJ accession No. D90905, PID; g1652389) (FIG. 3). As regards the other proteins, it exhibited homologies of 43–46% with the KASII gene derived from the castor bean and the KASI gene derived from barley and 35% with KASI derived from *E. coli*. These homologies of genes however could not distinguish which of KASI, II or III corresponds to the function of the ORF.

Example 3

Measurement of activity of KASII-like gene derived from *Anacystis nidulans* in *E. coli*

In order to specify the function of the above described gene, the expression in *E. coli* was tried. Firstly, in order to remove the excess DNA sequences upstream and downstream ORF, prepared was a DNA in which at the N terminal, Nde I site was introduced in the 5' side of the start codon (ATG) by DNA synthesis (Applied Biosystem Co.), while Hind III site was introduced immediately downstream the ORF.

1: 5'-CGCACATATGACTGAAACCGGACGCC (SEQ ID NO. 5)

2: 5'-CCGCAAGCTTGCAGCAGCGCGTACTGC (SEQ ID NO. 6)

PCR reaction was performed with both synthetic DNAs as a primer in the presence of pF as a template DNA. Regarding the reaction condition, the reaction was repeated 30 cycles according to the manual from Perkin-Elmer Co. with each cycle comprising the reaction at 94° C. (1 minute), 60° C. (1 minute) and 72° C. (2 minutes). The reaction product was cleaved with NdeI and Hind III, followed by cloning with pET17b preliminarily cleaved with the same restriction enzyme set as described above into *E. coli* strain DH5, which was then cloned into a strain BL21(DE3)pLysS (Novagen).

The recombinant of a latter *E. coli* strain was cultured (32° C) until the turbidity of the culture solution reached 0.5 OD at a wavelength of 600 nm in 75 ml of LB medium to which 100 µg/ml of ampicillin and 30 µg/ml of chloramphenicol had been added. IPTG was then added at a final concentration of 0.4 mM, and culturing was further continued for 2 hours. *E. coli* was recovered from the culture medium by centrifugation at 10,000× g for 10 minutes, and the cells were washed with 50 mM Tris HCl (pH 7.4) and frozen at −20° C. The cells were thawed in ice with a solution consisting of 20 mM Tris HCl (pH 8.0), 20 mM dithiothreithol, 10 mM MgCl$_2$ and 1 μg/ml Dnase I. The mixture was centrifuged at 100,000× g at 4° C. for 1 hour, and the protein solution as the supernatant was subjected to SDS electrophoresis on a slab gel having a polyacrylamide concentration gradient from 10 to 20% followed by dying with Coomassie brilliant blue. As a result, the protein derived from *Anacystis nidulans* was detected as a protein having a molecular weight of about 50 kDa.

As for the fatty acid composition of *E. coli,* the fatty acids were recovered for analysis as the methyl esters from the cells cultured as described above. Methylation was carried out by heating about 5 mg of lipid together with 1 ml of 5% hydrochloric acid in anhydrous methanol in a sealed tube in boiling water for 4 hours, the reaction mixture was cooled by standing followed by extracting the fatty acid methyl esters with hexane. Methylated fatty acid esters were analyzed on a capillary column (polyester liquid phase; 10% EGSS-X, 175° C.) with a hydrogen flame ionization detector. Fatty acids were determined by comparing their relative retention times with those of standard methylated fatty acids. The results are listed in the following table.

| Fatty acid compositions in *E. coli* | | | | | | |
|---|---|---|---|---|---|---|
| Sample | 14:0 | 16:0 | 16:1 | 18:0 | 18:1 | 16:0 + 16:1/ 18:0 + 18:1 |
| Control | 2 | 37 | 21 | 1 | 38 | 1.49 |
| Recombinant #1 | 0 | 24 | 13 | 6 | 57 | 0.59 |
| Recombinant #2 | 0 | 21 | 11 | 7 | 62 | 0.46 |

As a result, it has been found that the fatty acids with 16 carbon atoms (16:0 and 16:1) were decreased, while the ratio of the fatty acids with 18 carbon atoms (18:0 and 18:1) was increased substantially.

Industrial Applicability

The DNA chain coding for protein which has a β-ketoacyl-ACP synthetase II enzyme activity represented by the enzyme KASII derived from *Anacystis nidulans* has been provided by the present invention. The gene coding for the enzyme protein of the present invention, as described above, is a gene of the enzyme KASII which has a remarkably high activity of converting a fatty acid (particularly, palmitic acid with C16) into an even longer fatty acid (particularly, stearic acid with C18), and is useful, by using transformation, for the improvement of the lipids of plants, the improvement of the lipids of microorganisms, particularly for the control of the ratio between fatty acids having 16 and 18 carbon atoms or for the increase of the content of unsaturated fatty acids.

What is claimed is:

1. An isolated nucleotide sequence encoding a protein having β-ketoacyl-ACP synthetase II activity, wherein the protein comprises the amino acid sequence of SEQ ID NO:2.

2. An isolated nucleotide sequence encoding a protein having β-ketoacyl-ACP synthetase II activity, wherein the protein is present in cyanobacterium, and the nucleotide sequence hybridizes to the complement of the isolated nucleotide sequence of claim 1 when the nucleotide sequence and the complement are:

(a) incubated together at 60° C. for 16 hours in a solution consisting of 5× SSC, 10 mM EDTA, 10× Denhardt solution, and 250 μg/ml of salmon sperm DNA, and (b) washed twice at 45° C. for 15 minutes with a solution consisting of 5× SSC and 0.1% SDS.

3. A protein encoded by the nucleotide sequence of claim 1 or 2.

4. A recombinant vector comprising the nucleotide sequence of claim 1 or 2.

5. A cell transformed with the nucleotide sequence of claim 1 or 2.

* * * * *